United States Patent
Kim et al.

(10) Patent No.: US 12,274,717 B2
(45) Date of Patent: Apr. 15, 2025

(54) PCNT AS A TARGET PROTEIN FOR TREATMENT OR DIAGNOSIS OF BRAIN-NERVOUS SYSTEM DISEASES

(71) Applicant: SUNGKWANG MEDICAL FOUNDATION, Seoul (KR)

(72) Inventors: Minyoung Kim, Seoul (KR); Jee In Choi, Seongnam-si (KR)

(73) Assignee: SUNGKWANG MEDICAL FOUNDATION, Seoul (KR)

( * ) Notice: Subject to any disclaimer, the term of this patent is extended or adjusted under 35 U.S.C. 154(b) by 731 days.

(21) Appl. No.: 16/477,443

(22) PCT Filed: Jan. 11, 2018

(86) PCT No.: PCT/KR2018/000539
§ 371 (c)(1),
(2) Date: Jul. 11, 2019

(87) PCT Pub. No.: WO2018/131909
PCT Pub. Date: Jul. 19, 2018

(65) Prior Publication Data
US 2019/0336541 A1    Nov. 7, 2019

(30) Foreign Application Priority Data
Jan. 11, 2017  (KR) ................. 10-2017-0004167

(51) Int. Cl.
| | | |
|---|---|---|
| A61K 35/51 | (2015.01) | |
| A61K 9/00 | (2006.01) | |
| A61K 38/18 | (2006.01) | |
| C12Q 1/6827 | (2018.01) | |
| C12Q 1/6851 | (2018.01) | |
| G01N 33/50 | (2006.01) | |

(52) U.S. Cl.
CPC ............ *A61K 35/51* (2013.01); *A61K 9/0019* (2013.01); *A61K 38/18* (2013.01); *C12Q 1/6827* (2013.01); *C12Q 1/6851* (2013.01); *G01N 33/5023* (2013.01); *G01N 2500/04* (2013.01); *G01N 2500/10* (2013.01)

(58) Field of Classification Search
CPC .............. A61K 35/51; A61K 38/1816; G01N 2500/10; G01N 33/6896
See application file for complete search history.

(56) References Cited

U.S. PATENT DOCUMENTS

| | | | |
|---|---|---|---|
| 8,279,434 B2 | 10/2012 | Mertsching et al. | |
| 9,795,637 B1 * | 10/2017 | Sanberg | .............. A61P 17/02 |
| 2010/0322899 A1 * | 12/2010 | Kraus | .................. A61K 38/18 |
| | | | 424/85.1 |

FOREIGN PATENT DOCUMENTS

| | | | |
|---|---|---|---|
| JP | 2005-287430 | 10/2005 | |
| JP | 2008-48733 A | 3/2008 | |
| JP | 2014-176389 A | 9/2014 | |
| KR | 10-2013-0087432 A | 8/2013 | |
| KR | 10-2013-0093890 A | 8/2013 | |
| KR | 10-1493336 B1 | 2/2015 | |
| WO | WO 2008/121120 A1 | 10/2008 | |
| WO | WO-2013020136 A2 * | 2/2013 | ............. A61K 35/28 |
| WO | WO 2014/124174 A2 | 8/2014 | |

OTHER PUBLICATIONS

Kanof et al. Preparation of Human Mononuclear Cell Populations and Subpopulations; Current Protocols in Immunology, Suppl. 1:Unit 7.1, pp. 1-9. (Year: 1996).*
Li et al. Comparison of the Efficacy of Cord Blood Mononuclear Cells (MNCS) and CD34+ Cells for the Treatment of Neonatal Mice With Cerebral Palsy; Cell Biochem Biophys, vol. 70, pp. 1539-1544. (Year: 2014).*
Jensen et al. First Autologous Cell Therapy of Cerebral Palsy Caused by Hypoxic-Ischemic Brain Damage in a Child After Cardiac Arrest—Individual Treatment With Cord Blood; Case Reports in Transplantation, vol. 2013, pp. 1-6. (Year: 2013).*
Anonymous, Pericentrin Isoform X3 [*Homo sapiens*], downloaded from http://www.ncbi.nlm.nih.gov/gene?Db=gene&Cmd=DetailsSearch &Term=5116 on May 12, 2022. (Year: 2022).*
Anitha, A. et al., "Gene and Expression Analyses Reveal Enhanced Expression of Pericentrin 2 (PCNT2) in Bipolar Disorder," Biological Psychiatry, vol. 63, 2008, pp. 678-685.
Numata, S. et al., "Positive association of the pericentrin (PCNT) gene with major depressive disorder in the Japanese population," J Psychiatry Neurosci, vol. 34, No. 3, 2009, pp. 195-198.
Liu, Q. et al., "Pericentrin contains five NESs and an NLS essential for its nucleocytoplasmic trafficking during the cell cycle," Cell Research, vol. 20, No. 8, Aug. 2010, pp. 948-962.
Unal, S. et al., "Striking Hematological Abnormalities in Patients With Microcephalic Osteodysplastic Primordial Dwarfism Type II (MOPD II): A Potential Role of Pericentrin in Hematopoiesis," Pediatric Blood & Cancer, vol. 61, No. 2, Feb. 2014, pp. 1-4.

(Continued)

*Primary Examiner* — Jeanette M Lieb
*Assistant Examiner* — Paul C Martin
(74) *Attorney, Agent, or Firm* — Oblon, McClelland, Maier & Neustadt, L.L.P.

(57) ABSTRACT

Provided are a pharmaceutical composition for preventing or treating a central nervous system disease including, as an active ingredient, cord blood or cord blood-derived cells expressing or secreting pericentrin (PCNT), a composition or kit for diagnosing a central nervous system disease including an agent for measuring a level of PCNT protein, a method of analyzing information required for diagnosing a central nervous system disease using PCNT protein, and a method of screening a candidate substance for a therapeutic agent to treat a central nervous system disease. By using the composition including cord blood or cord blood-derived cells expressing or secreting PCNT, central nervous system diseases may be efficiently prevented or treated. Furthermore, the PCNT protein may be used as a target for diagnosing a central nervous system disease at an early stage and for developing a therapeutic agent for a central nervous system disease.

3 Claims, 9 Drawing Sheets
Specification includes a Sequence Listing.

(56) References Cited

OTHER PUBLICATIONS

Nolte, F. et al., "Centrosome aberrations in bone marrow cells from patients with myelodysplastic syndromes correlate with chromosomal instability," Annals of Hematology, vol. 92, 2013, pp. 1325-1333.

Delaval, B. et al., "Pericentrin in cellular function and disease", The Journal of Cell Biology, vol. 188, No. 2, 2010, 10 pages.

Office Action issued Jun. 16, 2020 in corresponding Japanese Patent Application No. 2019-537788 (with English Translation), 12 pages.

K. Min et al., "Umbilical Cord Blood Therapy Potentiated with Erythropoietin for Children with Cerebral Palsy: A Double-blind, Randomized, Placebo-Controlled Trial", Stem Cells, 2013, 31, pp. 581-591.

Office Action issued Nov. 1, 2022, in corresponding Japanese Patent Application No. 2021-062910 (with English-language Translation).

Akihiko Taguchi, et al., "Administration of DC34+ cells after storoke enhances neurogenesis via angiogenesisin a mouse model", *JCI The Journal of Clinical Investigation*, 2004, 114(3), pp. 330-338.

Lei Huang, et al., "Intraarterial transplantation of human umbilical cord blood mononuclear cells in hyperacute stroke improves vascular function" *Stem Cell Research & Therapy*, Mar. 22, 2017, 8,74.

Final Japanese Office Action issued on May 9, 2023 in Japanese Patent Application No. 2021-062910 (with English translation), 4 pages.

Japanese Office Action issued on May 9, 2023 in Japanese Patent Application No. 2021-062910 (with English translation), 5 pages.

Japanese Office Action issued Aug. 20, 2024 in Japanese Patent Application No. 2023-145820 (with English Translation), 8 pages.

"Monocyte", Nanzando Medical Dictionary, Eighteenth Edition, 1998, pp. 1325 (reference previously filed, now submitting English Translation).

* cited by examiner

PCNT AS A TARGET PROTEIN FOR TREATMENT OR DIAGNOSIS OF BRAIN-NERVOUS SYSTEM DISEASES

TECHNICAL FIELD

The present disclosure relates to a pharmaceutical composition for preventing or treating central nervous system (brain-nervous system) diseases, the pharmaceutical composition including, as an active ingredient, cord blood or cord blood-derived cells expressing or secreting pericentrin (PCNT), a composition or kit for diagnosing a central nervous system disease including an agent for measuring a level of PCNT protein, a method of analyzing information required for diagnosing a central nervous system disease using PCNT protein, and a method of screening candidate substances for a therapeutic agent to treat a central nervous system disease.

BACKGROUND ART

The central nervous system is a body-controlling system including the brain, the spinal cord, cranial nerves, spinal nerves, the autonomic nervous system, and the like. Examples of a central nervous system disease may include cerebral palsy, brain damage, traumatic brain injury, ischemic brain injury, concussion, cerebral contusion, cerebral apoplexy, cerebral infarction, cerebral hemorrhage, Parkinson's disease, Alzheimer's disease, Huntington's chorea, stroke, dementia, Lou Gehrig's disease, Pick's disease, Creutzfeldt-Jakob disease, amyotrophic lateral sclerosis, primary lateral sclerosis, degenerative ataxia, multiple sclerosis, nervous system dysfunction, hypomnesis, epilepsy, encephalitis, prion disease, and neuropathy. Brain damage (or brain injury) refers to a state including abnormal behavior or dysfunction caused by disorders in nervous tissue of the brain occurring due to a wide range of internal and external factors. Brain damage may be caused by open head injury, closed head injury, deceleration injury, exposure to toxic substances, lack of oxygen, tumors, infections, and cerebrovascular diseases such as stroke.

Cerebral palsy is a collective term referring to a syndrome with similar clinical symptoms, rather than a disease, and the clinical symptoms include motor and posture dysfunction resulting from non-progressive disturbance or injury occurring in a premature brain. Cerebral palsy is a disorder that causes problems, such as in the ability to control muscles or to maintain posture while walking, caused by injury to a developing brain, and brain damage often occurs before or after childbirth or during childbirth but may also occur at any time during pregnancy or childhood.

Although damage to the brain is non-progressive, symptoms of neuromotor disorders and musculoskeletal disorders vary over time, and thus the most appropriate rehabilitation treatment for changing clinical symptoms needs to be provided via periodic examinations. Although there are other treatments, novel and effective treatments have not been developed.

A potential effect of stimulating brain plasticity on treatment of cerebral palsy has been reported and the stimulation of brain plasticity has a positive effect on patients with brain damage. Cell therapy exists as a method of stimulating the potential for brain plasticity.

Korean Patent No. 1493336 (Patent Document 1) provides a use of oligodendrocyte progenitor cells as a cell therapeutic agent for central nervous system diseases and discloses a composition for treating central nervous system diseases including, as an active ingredient, oligodendrocyte progenitor cells, which are stem cells transformed with an expression vector including a nucleic acid molecule encoding the Olig2 gene.

Meanwhile, directly transplanted stem cells including mesenchymal stem cells may fail to differentiate and survive in vivo, and they are difficult to quantitatively administer, thus making them difficult to use as cell therapeutic agents. Therefore, there is a need to develop a cell therapeutic agent having therapeutic effects on motor development and cognitive development without causing rejection in vivo.

DESCRIPTION OF EMBODIMENTS

Technical Problem

Thus, the present inventors have conducted research to investigate cord blood as a cell therapeutic agent to treat a central nervous system disease and have found pericentrin (PCNT) protein as a target protein for treating or diagnosing a central nervous system disease, thereby completing the present disclosure.

Provided is a pharmaceutical composition for preventing or treating a central nervous system disease including, as an active ingredient, cord blood or cord blood-derived cells expressing or secreting PCNT.

Provided is a composition or kit for diagnosing a central nervous system disease including an agent for measuring a level of PCNT protein or mRNA of a gene thereof.

Provided is a method of analyzing information required for diagnosing a central nervous system disease, the method including: measuring an expression level or activity level of PCNT protein or a gene thereof in a sample isolated from an individual; and comparing the measured expression level or activity level with an expression level or activity level of PCNT protein measured in a control sample isolated from a normal individual.

Provided is a method of screening a candidate substance for a therapeutic agent to treat a central nervous system disease, the method including: contacting cells expressing PCNT protein with a test substance in vitro; measuring an expression level or activity of the PCNT protein in the cell; and, as a result of comparing the measured expression level or activity of the PCNT protein with an expression level or activity of the PCNT protein measured in a control group, selecting the test substance which increases the expression level or activity of the PCNT protein as the candidate substance for a therapeutic agent to treat the central nervous system disease.

Solution to Problem

According to an aspect of the present disclosure, a pharmaceutical composition for preventing or treating a central nervous system disease includes, as an active ingredient, cord blood or cord blood-derived cells expressing or secreting pericentrin (PCNT).

According to another aspect of the present disclosure, provided is a pharmaceutical composition for preventing or treating a central nervous system disease including, as an active ingredient, PCNT protein or an active fragment thereof.

The term "pericentrin (PCNT)", binding to calmodulin, refers to a protein expressed in a centrosome and constitutes the centrosome together with a centriole. PCNT protein is known to play an important role in cell division (Liu Q et al., August 2010, Cell Research. 20 (8): 948-62.). Mental illnesses caused by abnormalities of this protein have been reported (Unal S et al., February 2014, Pediatric Blood & Cancer. 61 (2): 302-5.). Higher expression levels of the PCNT protein were observed in cord blood than those of plasma of normal individuals and lower expression levels of the PCNT protein was observed in plasma of patients with cerebral palsy than normal individuals. Also, it was confirmed that the expression levels of the PCNT protein increased in patients with cerebral palsy by cell therapy of cord blood when compared with those of the PCNT protein before the cell therapy. The results indicate that the PCNT protein may be used as a diagnosis marker for diagnosing central nervous system diseases such as cerebral palsy and the PCNT protein is related to prevent or treat the central nervous system diseases. Therefore, cord blood or cord blood-derived cells having a high expression level of the PCNT protein may be used to prevent or treat central nervous system diseases.

The PCNT protein may be secreted from cord blood or cord blood-derived cells. Also, the PCNT protein may be derived from mammals, e.g., humans, monkeys, or rodents. According to an embodiment, the PCNT protein may have an amino acid sequence of SEQ ID NO: 1 (GenBank Accession No. XP_005261181).

According to an embodiment, the central nervous system disease may be a central nervous system disease in which the expression of PCNT is reduced, compared to normal individuals. According to another embodiment, the central nervous system disease may include diseases caused by abnormalities or disorders of a part of or the entire brain, spinal cord, cranial nerves, spinal nerves, autonomic nervous system, and the like constituting the central nervous system. According to another embodiment, the central nervous system disease may be a brain damage disease. According to another embodiment, the central nervous system disease may be a nerve damage disease. According to another embodiment, the central nervous system disease may be selected from, but is not limited to, cerebral palsy, brain damage, traumatic brain injury, ischemic brain injury, concussion, cerebral contusion, cerebral apoplexy, cerebral infarction, cerebral hemorrhage, Parkinson's disease, Alzheimer's disease, Huntington's chorea, stroke, dementia, Lou Gehrig's disease, Pick disease, Creutzfeld-Jakob disease, amuotrophic lateral sclerosis, primary lateral sclerosis, degenerative ataxia, multiple sclerosis, nervous system dysfunction, hypomnesis, epilepsy, encephalitis, prion disease, and neuropathy. According to another embodiment, the central nervous system disease may be cerebral palsy.

The term "cerebral palsy" refers to a syndrome having clinical symptoms of motor and posture dysfunction caused by non-progressive disturbance or injury occurring in a premature brain due to various reasons during childbirth or after birth.

The term "cord blood" refers to blood remaining in placenta or umbilical cord. Cord blood includes hematopoietic stem cells such as leukocytes, erythrocytes, and platelets, and various other stem cells producing cartilage, bones, fats, muscles, and nerves in large quantities. The term "stem cell" refers to a undifferentiated cell in a primordial state and capable of differentiating into any organ and includes two types of stem cells: embryonic stem cells and adult stem cells. A stem cell derived from cord blood may be an adult stem cell such as mesenchymal stem cell (MSC). The cord blood may be obtained from an umbilical cord after childbirth. As the cord blood, a leukocyte concentrate from which erythrocytes and plasma have been removed may be used. The leukocyte concentrate of the cord blood may include various cord blood-derived cells such as hematopoietic stem cells, monocytes, neutrophils, B-lymphocytes, T-lymphocytes, CD4 T cells, CD8 T cells, NK cells, peripheral blood mononuclear cells (PBMC), platelets, lymphocytes, tonsils, bone marrow stromal cells, and bone marrow mesenchymal stem cells.

According to an embodiment, the cord blood may be autologous cord blood or allogeneic cord blood. The allogeneic cord blood may be cord blood of a family member such as a brother or a parent.

According to an embodiment, the cord blood-derived cells may be hematopoietic stem cells. According to another embodiment, the cord blood-derived cells may be cells expressing or secreting PCNT. According to another embodiment, the cord blood-derived cells may be selected from, but not limited to, monocytes, B-lymphocytes, CD4 T cells, CD8 T cells, NK cells, peripheral blood mononuclear cells, platelets, and lymphocytes. According to another embodiment, the cord blood-derived cells may be peripheral blood mononuclear cells. According to another embodiment, the cord blood-derived cells may be genetically engineered to express or secrete PCNT or increase the expression level of PCNT.

The pharmaceutical composition may further include erythropoietin (EPO). The erythropoietin may be a hormone regulating production of erythrocytes in bone marrow. When erythropoietin is administered in combination with cord blood or cord blood-derived cells, the therapeutic effect of the cord blood may be enhanced, thereby further improving motor and cognitive function of patients.

The term "treatment" refers to or includes alleviating, inhibiting the progress of, or preventing a disease, disorder, or condition, or at least one symptom thereof, and the term "active ingredient" or "pharmaceutically effective amount" refers to an amount of a composition used while performing a process according to the present disclosure sufficient to alleviate, inhibit the progress of, or prevent the disease, disorder, or condition, or at least one symptom thereof.

The terms "administering", "introducing", and "transplanting" are interchangeably used and may refer to placement of a composition according to an embodiment into an individual by a method or route which results in at least partial localization of the composition at a desired site. According to an embodiments, the composition may be administered by any appropriate route of delivering cells of the composition, at least portions of the cells, or products derived from the cells into a desired position in a living individual. The cells may survive for a short time, e.g., several hours to 24 hours or for a long time, e.g., several days to several years after administration into the individual.

The pharmaceutical composition may further include a pharmaceutically acceptable carrier or diluent. The pharmaceutically acceptable carrier or diluent may be well known in the art. The carrier or the diluent may be lactose, dextrose, sucrose, sorbitol, mannitol, starch, acacia rubber, calcium phosphate, alginate, gelatin, calcium silicate, micro-crystalline cellulose, polyvinyl pyrrolidone, cellulose, water (e.g., saline solution and sterile water), syrup, methyl cellulose, methylhydroxy benzoate, propylhydroxy benzoate, talc, magnesium stearate, and mineral oil, linger solution, buffer solution, maltodextrin solution, glycerol, ethanol, dextran, albumin, or any combination thereof. The pharmaceutical composition may further include a lubricant, a humectant, a sweetener, a flavoring agent, an emulsifier, a suspension, or a preservative.

The pharmaceutical composition may be formulated with a pharmaceutically acceptable carrier and/or excipient into a unit dosage form or a multiple dosage form by a well-known method in the art. In this regard, the formulation may be a solution in oil or aqueous medium, a suspension, a syrup, an emulsifying solution, an extract, a powder, a granule, a tablet, or a capsule and may further include a dispersant or a stabilizer. The aqueous medium may include a saline solution or a phosphate buffer solution (PBS). The pharmaceutical composition according to an embodiment may be formulated into in the form of an oral or parenteral administration, preferably, in the form of a parenteral administration. In general, a sterile solution of an active ingredient is prepared and a buffer for adjusting the pH is added to the solution for intramuscular, intraperitoneal, transdermal, and intravenous administration. For the intravenous administration, an isotonic agent may further be added to a preparation for isotonicity.

The pharmaceutical composition according to an embodiment may include cord blood-derived cells, as nucleated cells, of at least $1\times10^7$ cells/kg, particularly, at least $2\times10^7$ cells/kg, at least $3\times10^7$ cells/kg, in the range of $3\times10^7$ cells/kg to $10\times10^7$ cells/kg, for example, in the range of $3\times10^7$ cells/kg to $5\times10^7$ cells/kg.

A daily dose (effective amount) of the pharmaceutical composition according to an embodiment may be about 0.01 ml to about 200 ml, particularly, about 0.01 ml to about 150 ml, about 0.01 ml to about 100 ml, about 0.1 ml to about 150 ml, about 0.1 ml to about 100 ml, about 1 ml to about 100 ml, about 1 ml to about 50 ml, about 5 ml to about 50 ml, or about 10 ml to about 40 ml, for example, 15 ml to 30 ml. If required, the overall dose of the composition may be reduced by appropriately concentrating the cord blood. However, a prescribed dosage may vary according to various factors such as formulation method, administration route, age, weight, and gender of a patient, pathological conditions, diet, duration of administration, route of administration, excretion rate, susceptibility to reaction, and the dosage may be appropriately adjusted by those or ordinary skill in the art in consideration of these factors. Administration frequency may be once, or twice or more within the range of clinically acceptable side effects, and the site of administration may be one, two or more sites, every day or at every 2 or 5 days for a total duration of 1 day to 30 days for each treatment. If required, the same treatment may be repeated after a predetermined period. For animals other than humans, a dosage that is the same as that of per kg in a human, or a dosage that is determined by, for example, conversion based on the volume ratio (e.g. average value) of organs (e.g. heart) of the target animal and a human, may be administered. Available administration routes may include parenteral administration (e.g., subcutaneous, intramuscular, intra-arterial, intraperitoneal, transdermal, or intravenous administration), topical administration (including transdermal administration), and injection, or insertion of or a transplantable device or a substance. As a target animal for therapy according to an embodiment, a human and a mammal of interest may be exemplified For example, the target may be a human being, a monkey, a mouse, a rat, a rabbit, sheep, a cow, a dog, a horse, a pig, or the like.

Provided is a composition or kit for diagnosing a central nervous system disease including an agent for measuring a level of PCNT protein or mRNA of a gene thereof.

The PCNT protein and central nervous system diseases are as described above.

According to an embodiment, it was confirmed that the expression levels of the PCNT protein in patients with cerebral palsy were lower than those in plasma of normal individuals. Thus, the onset or progression of a central nervous system disease such as cerebral palsy may be diagnosed by measuring the expression level or activity of the PCNT protein and comparing the measured value with that of a sample of a normal individual. Therefore, the PCNT protein may be a diagnosis marker of a central nervous system disease, e.g., cerebral palsy.

The term "diagnosis" refers to identifying the presence or characteristics of a pathological condition. Thus, the "diagnosis of a central nervous system disease" may mean identifying the onset or possibility of onset of a central nervous system or predicting the risk of the onset.

The term "diagnosis marker" refers to a substance capable of diagnosing the onset of a central nervous system disease or the possibility of the onset.

The agent for measuring the protein may be an antibody specifically binding to the PCNT protein or a fragment thereof.

The agent for measuring the level of mRNA of the gene may include a primer or probe specifically binding to a nucleic acid encoding the PCNT protein or the fragment thereof.

The antibody specifically binding to the PCNT protein may be easily prepared from the PCNT protein having a known amino acid sequence by those of ordinary skill in the art using a known method. The antibody specifically binding to the PCNT protein may include a monoclonal antibody, a polyclonal antibody, and a recombinant antibody. The antibody may be in a complete form having a full length of two heavy chains and two light chains, as well as a functional fragment having at least antigen-binding function such as Fab, F(ab'), F(ab')$_2$, and Fv.

Also, those of ordinary skill in the art may design a primer or probe the specifically amplifies or recognize a certain region from a known sequence of the PCNT gene.

The term "primer", referring to a nucleic acid strand, has a short free 3' hydroxyl group, is capable of forming base pairs with a complementary template, serves as a starting point of replication of a template strand, and has a length of 7 to 50 nucleotides. The primer is generally synthesized but a natural nucleic acid may be used therefor. The sequence of the primer does not necessarily have to be exactly the same as that of the template, but may be complementary sufficient to be hybridized with the template. The primer may initiate DNA synthesis in the presence of a reagent for polymerization (i.e., DNA polymerase or reverse transcriptase) and four different nucleoside triphosphates in an appropriate buffer solution at an appropriate temperature. PCR conditions and lengths of sense and antisense primers may be modified based on technologies well known in the art. Thus, a central nervous system disease may be diagnosed by perform PCR amplification using sense and antisense primers of a nucleotide sequence of the PCNT gene.

The term "probe" refers to a nucleic acid fragment such as RNA or DNA having a short nucleotide sequence of several nucleotides to a long nucleotide sequence of several hundreds of nucleotides and capable of specifically binding to mRNA. Because the probe is labeled, the presence of a certain mRNA may be identified. The probe may be prepared in the form of an oligonucleotide probe, a single stranded DNA probe, a double stranded DNA probe, an RNA probe, and the like. Appropriate probes may be selected and hybridization conditions may be modified based on technologies well known in the art. Thus, a central nervous system disease may be diagnosed by performing hybridization using a probe complementary to a nucleotide sequence of the PCNT gene.

The primer or probe may be chemically synthesized by a phosphonamidite solid support method, or any other known methods. Such nucleic acid sequences may incorporate additional features that do not change basic properties. Examples of the additional features that may be incorporated include, but are not limited to, methylation, capping, substitution of one or more nucleic acids with homologues, or modifications between nucleic acids.

The kit may be an RT-PCR kit, a microarray chip kit, or a protein chip kit.

The kit may further include one or more other components suitable for an assay method. When the assay method is RT-PCR, the kit may further include a necessary container, a reaction buffer, deoxynucleotide (dNTP), a DNA polymerase for PCR, and a reverse transcriptase in addition a primer set specific to the PCNT protein. Also, when the assay method is ELISA, the kit may further include a reagent for detecting bound antibody, e.g., a secondary antibody, a chromophore, an enzyme, and a substrate thereof.

Provided is a method of analyzing information required for diagnosing a central nervous system disease, the method including: measuring an expression level or activity level of PCNT protein or a gene thereof in a sample separated from an individual; and comparing the measured expression level or activity level with that of PCNT protein measured in a control sample.

The PCNT protein and central nervous system diseases are as described above.

The method includes measuring an expression level or activity level of PCNT protein or a gene thereof in a sample separated from an individual.

The term "individual" refers to an individual used to identify the onset or possibility of the onset of a central nervous system disease or predict the risk of the onset. The individual may be any animal which may undergo the central nervous system disease without limitation, particularly, a mammal, e.g., a human being (*Homo sapiens*).

The sample may include, but is not limited to, tissue, cells, whole blood, serum, plasma, saliva, sputum, cerebrospinal fluid, urine, and the like isolated from the individual. According to an embodiment, the sample may be plasma.

The measuring of the expression level of the PCNT protein or the gene thereof may be performed by measuring an amount of mRNA of the PCNT gene or the PCNT protein.

The measuring of the expression level of the PCNT protein, i.e., the level of mRNA, may be performed by, but is not limited to, RT-PCR, competitive RT-PCR, Real-time RT-PCR, RNase protection assay (RPA), Northern blotting, DNA chip, and the like.

The measuring of the activity level of the PCNT protein may be performed by, but is not limited to, Western blotting, magnetic bead-antibody immunoprecipitation, ELISA, mass spectrometry, radioimmunoassay, immunoprecipitation, and the like.

The method includes comparing the measured expression level or activity level with an expression level or activity level of PCNT protein measured in a control sample. When the expression level or activity level of the PCNT protein is lower in the sample than that of the PCNT protein measured in the control sample obtained from the normal individual, it may be determined that the sample has a high probability of onset or progression of a central nervous system disease. Thus, the method may further include determining the sample as having a central nervous system disease when the measured expression level or activity level is lower than the expression level or activity level measured in the control sample.

Provide is a method of screening a candidate substance for a therapeutic agent to treat a central nervous system disease, the method including: contacting cells expressing PCNT protein with a test substance in vitro; measuring an expression level or activity of the PCNT protein in the cell; and selecting the test substance as the candidate substance for a therapeutic agent to treat the central nervous system disease, when the test substance increases the expression level or activity of PCNT protein by comparing the measured expression level or activity of the PCNT protein with an expression level or activity of the PCNT protein measured in a control group.

The PCNT protein and central nervous system diseases are as described above.

Increases in the expression levels of the PCNT protein by cell therapy of cord blood were confirmed in patients with cerebral palsy when compared with those of the PCNT protein before the cell therapy, and alleviation of cerebral palsy thereby was also confirmed. Thus, a substance capable of specifically increasing the expression or activity level of the PCNT protein may have a therapeutic effect on the central nervous system disease such as cerebral palsy. Such an effect shows that the PCNT protein or the gene thereof is a target of treatment of the central nervous system disease such as cerebral palsy.

The method includes contacting cells expressing PCNT protein with a test substance in vitro.

The cells expressing the PCNT protein may be, but is not limited to, blood cells, brain cells, and the like.

The contacting of the cells with the test substance may be performed by transfection, transformation, or injection.

The contacting of the cells with the test substance may be performed in a medium capable of maintaining the growth of the cells.

The method includes measuring an expression level or activity of the PCNT protein in the cells.

The measuring may be performed by an antibody specifically recognizing the PCNT protein or a fragment thereof, or a primer or probe specifically recognizing a nucleic acid encoding the PCNT protein or the fragment thereof.

The measuring of the expression level may be performed by measuring an amount of mRNA of the PCNT gene or the PCNT protein.

The measuring of the mRNA may be performed by, but is not limited to, RT-PCR, competitive RT-PCR, Real-time RT-PCR, RNase protection assay (RPA), Northern blotting, DNA chip, and the like.

The amount of the protein may be measured by Western blotting, magnetic bead-antibody immunoprecipitation, ELISA, mass spectrometry, radioimmunoassay, immunoprecipitation, and the like, without being limited thereto.

The method includes selecting the test substance as the candidate substance for a therapeutic agent to treat the central nervous system disease, when the test substance increasing the expression level or activity of PCNT protein by comparing the measured expression level or activity of the PCNT protein with an expression level or activity of the PCNT protein measured in a control group.

When the expression level or activity level of the PCNT protein is further increased after treating with the test substance, the test substance may be selected as a substance used to treat the central nervous system disease by increasing expression or activity of the PCNT protein.

The control group includes cells under the same conditions except that the cells were not brought in contact with the test substance.

Advantageous Effects of Disclosure

By using the composition including cord blood or cord blood-derived cells expressing or secreting PCNT, central nervous system diseases may be efficiently prevented or treated. Also, the PCNT protein may be used as a target for diagnosing a central nervous system disease at an early stage and for developing a therapeutic agent for the central nervous system disease.

MODE OF DISCLOSURE

Figure 1:
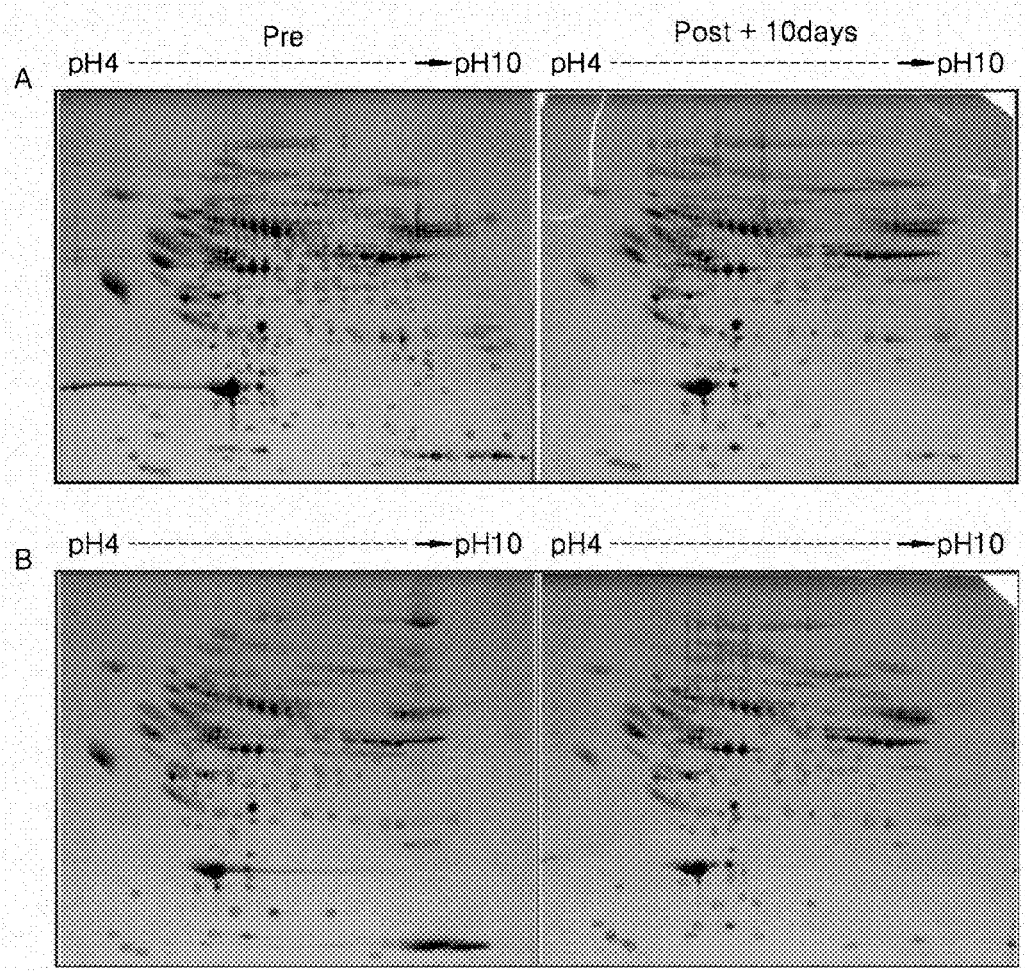
FIG. 1A shows two-dimensional gel electrophoresis (2DE) results of Experiment 1 (analysis of sample of infant Nos. 4, 9, and 10) to identify changes of proteins contained in plasma before cord blood therapy (Pre) and at 10 days after therapy (Post+10 days).
FIG. 1B shows 2DE results of Experiment 2 (analysis of samples of infant Nos. 6, 7, and 8) to identify changes of proteins contained in plasma before cord blood therapy (Pre) and at 10 days after therapy (Post+10 days).

Hereinafter, the present disclosure will be described in more detail with reference to the following examples. However, these examples are for illustrative purposes only and are not intended to limit the scope of the present disclosure.

Example 1: Screening of Protein with Changed Expression Level after Cord Blood Therapy Blood was taken from infants with cerebral palsy before and after cord blood cell therapy and changes in certain proteins present in plasma were observed. In the cord blood cell therapy, a leukocyte concentrate, which was prepared by removing erythrocytes and plasma from the blood and cryopreserved, was used as the cord blood. Before the therapy, the cryopreserved leukocyte concentrate was thawed in a water bath at 37° C. and washed with a diluted solution including 10% dextran-40 (100 g of dextran-40/1 l of water) and 5% albumin (50 g of albumin/1 l of water) in an equal volume. The washed leukocyte concentrate was suspended in 10 ml of a mixed solution of 10% dextran-40 and 5% albumin diluted in an equal volume, such that a minimum number of nucleated cells was $3 \times 10^7$ cells/kg, and the suspension was administered via intravenous injection at a dose of 15 ml to 30 ml.

Preparation of Plasma Sample for Screening

Table 1 shows disease names of selected infants with cerebral palsy and whether treated with cord blood cell therapy for screening of proteins contained in plasma. About 1 cc to about 3 cc of blood of the infants with cerebral palsy listed in Table 1 was taken in an EDTA-tube and centrifuged at a rate of 2000 rpm. In this case, the blood was separated into a bottom layer containing erythrocytes, an intermediate layer containing monocytes, and a top layer containing plasma. Only the plasma is separated from the divided blood and cryopreserved in a cryocooler at −80° C.

TABLE 1

| No. | Gender | Age (Month) | Allogeneic cord blood therapy | Autologous cord blood therapy | Cyclosporin | Diagnosis |
|---|---|---|---|---|---|---|
| 1 | Male | 123 | | ○ | | Delayed milestone |
| 2 | Male | 42 | | ○ | | Mitochondrial myopathy, NEC |
| 3 | Male | 20 | ○ | | ○ | Cerebral palsy |
| 4 | Male | 137 | ○ | | ○ | Cerebral palsy |
| 5 | Female | 70 | ○ | | ○ | Delayed milestone |
| 6 | Male | 13 | | ○ | | Cerebral palsy |
| 7 | Female | 42 | ○ | | ○ | Cerebral palsy |
| 8 | Female | 20 | ○ | | ○ | Cerebral palsy |
| 9 | Female | 81 | ○ | | ○ | Cerebral palsy |
| 10 | Female | 141 | ○ | | ○ | Delayed milestone |

A. Screen of Protein in Plasma Before and after Cord Blood Cell Therapy

2-Dimensional gel Electrophoresis (2DE) was used to identify changes of certain proteins present in the plasma separated according to Example 1-1 described above. The 2DE, image analysis, and qualitative analysis of the prepared samples were conducted by researchers of Yonsei Proteome Research Center, Yonsei University.

6 infants with cerebral palsy whose symptoms have been alleviated by the cord blood therapy, i.e., infant Nos. 4, 6, 7, 8, 9, and 10, were selected from the 10 infants with cerebral palsy listed in Table 1 and subjected to experiments.

Table 2 shows information on samples for experiments for screening of proteins contained in plasmas of the 6 infants whose symptoms have been alleviated by the cord blood therapy. In Experiment 1, a mixture of the plasmas of infant Nos. 4, 9, and 10 was used as plasma before the cord blood therapy, and the plasma of infant No. 4 was used as a plasma sample at 10 days after the cord blood therapy. In Experiment 2, a mixture of the plasmas of infant Nos. 6, 7, and 8 was used as plasma before the cord blood therapy, and the plasma of infant No. 6 was used as plasma at 10 days after the cord blood cell therapy.

TABLE 2

| | Experiment 1 | | Experiment 2 | |
|---|---|---|---|---|
| | Before cord blood therapy | At 10 days after cord blood therapy | Before cord blood therapy | At 10 days after cord blood therapy |
| Sample | Mixture of plasmas of infant Nos. 4, 9, and 10 | Plasma of infant No. 4 | Mixture of plasmas of infant Nos. 6, 7, and 8 | Plasma of infant No. 6 |

FIG. 1A shows 2-dimensional gel electrophoresis (2DE) results of Experiment 1 (analysis of the sample of infant Nos. 4, 9, and 10) to identify changes of proteins contained in plasma before the cord blood therapy (Pre) and at 10 days after the therapy (Post+10 days). FIG. 1B shows 2DE results of Experiment 2 (analysis of the sample of infant Nos. 6, 7, and 8) to identify changes of proteins contained in plasma before the cord blood therapy (Pre) and at 10 days after the therapy (Post+10 days). The horizontal axis represents pH, and the vertical axis represents size of protein.

Table 3 shows proteins, expressions of which increased more than three times in the plasmas of infants whose symptoms have been alleviated after the cord blood therapy, as a result of qualitative analysis of each protein according to the 2DE results. Because two points were observed for alpha-2-macroglobulin isoform, which is generally contained in plasma, it may be considered that the protein was not completely removed from the samples in the experiments. The protein exhibiting 626 points is considered as a fragment binding to fibrinogen, and it is also considered that this result was obtained because fibrinogen was not completely removed from the plasma. Thus, pericentrin (PCNT) was confirmed as a protein, the level of which increases in plasma after the cord blood therapy.

TABLE 3

| Level of protein | Spot No. | Name of protein (gray p > 0.05) | Score* | gi No. | Molecular weight (Mw) |
|---|---|---|---|---|---|
| Increase | 62 | alpha-2-macroglobulin isoform X1 | 72 | gi\|578822814 | 168914 |
| | 84 | pericentrin isoform X2 | 102 | gi\|530419252 | 368506 |
| | 92 | alpha-2-macroglobulin isoform X1 | 168 | gi\|578822814 | 168914 |
| | 626 | a well-known structure of a truncated form of the staphylococcal complement inhibitor G binding to human C3c at a resolution of 3.4 Å, chain E | 106 | gi\|358009626 | 23690 |

*The scores are −10*Log(P), where P is a probability that the observed match is a random event. A protein score of 72 or more is significant ($p < 0.05$).

Example 2: Identification of Expression of PCNT in Infants with Cerebral Palsy Treated with Cord Blood Therapy 2-1. Preparation of Plasma Samples of Infants with Cerebral Palsy Table 4 shows a list of infants with cerebral palsy, types of treated cord blood, and information on whether erythropoietin (EPO) is injected. Cord blood of a brother or a family member was used as the allogeneic cord blood. Blood was taken from 13 infants with cerebral palsy listed in Table 4 and separated and only plasma was collected therefrom. The collected plasma was quantitated by the Bradford assay by diluting at 5:1 with a phosphate-buffered saline (PBS). 30 μg of the quantified protein was mixed with a sample buffer and boiled for 7 minutes and then spined down.

TABLE 4

| No. | Gender | Disease name | Autologous cord blood therapy (Auto UCB) | Allogeneic cord blood therapy (Allo UCB) | EPO injection |
|---|---|---|---|---|---|
| 1 | Female | Cerebral palsy | — | ○ | — |
| 2 | Male | Cerebral palsy | — | ○ | — |
| 3 | Female | Cerebral palsy | — | ○ | — |
| 4 | Male | Cerebral palsy | — | ○ | — |
| 5 | Male | Cerebral palsy | — | ○ | — |
| 6 | Female | Cerebral palsy | — | ○ | ○ |
| 7 | Female | Cerebral palsy | — | ○ | ○ |
| 8 | Male | Cerebral palsy | ○ | — | ○ |

TABLE 4-continued

| No. | Gender | Disease name | Autologous cord blood therapy (Auto UCB) | Allogeneic cord blood therapy (Allo UCB) | EPO injection |
|---|---|---|---|---|---|
| 9 | Male | Cerebral palsy | ○ | — | ○ |
| 10 | Male | Cerebral palsy | ○ | — | ○ |
| 11 | Male | Cerebral palsy | ○ | — | ○ |
| 12 | Male | Cerebral palsy | ○ | — | ○ |
| 13 | Male | Cerebral palsy | ○ | — | ○ |

2-2. Identification of Expression of PCNT Protein after Cord Blood Therapy

Expression of the PCNT protein was identified by Wester blotting after the cord blood therapy.

First, the plasma sample prepared according to Example 2-1 was sequentially seeded onto 8% SDS-polyacrylamide gel before and after the cord blood therapy. Protein was transferred from the gel to a nitrocellulose (NC) membrane and reacted with a PCNT antibody for 16 hours or more, and then the expression level of the PCNT was identified with bands before and after the cord blood therapy.

Figure 2:
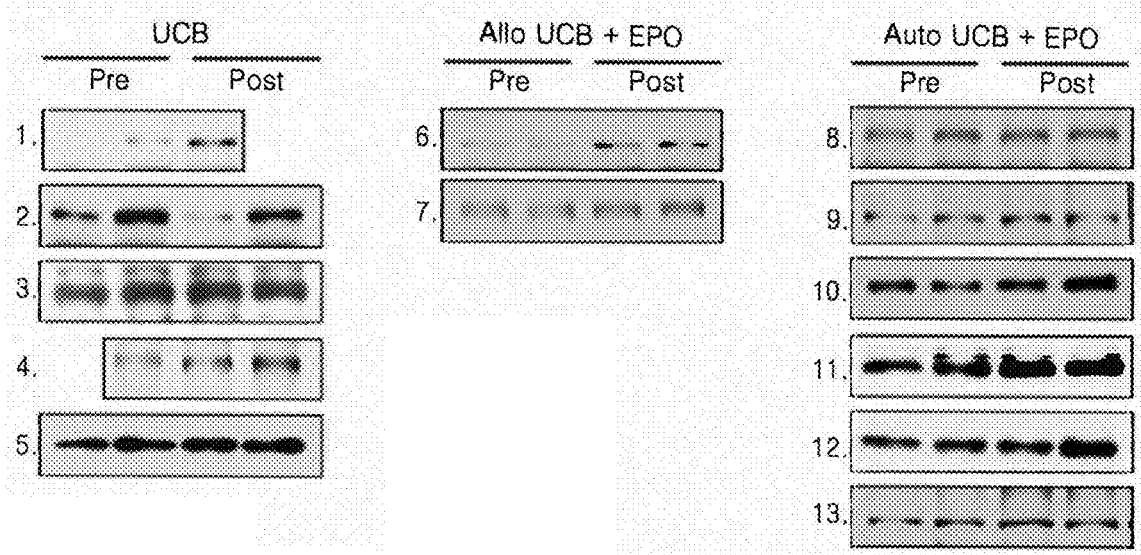
FIG. 2 shows Western blotting results of the plasma of 13 infants with cerebral palsy indicating the expression of PCNT protein before (Pre) and after (Post) cord blood therapy.

FIG. 2 shows Western blotting results of the plasma of 13 infants with cerebral palsy indicating the expression of PCNT protein before (Pre) and after (Post) of the cord blood therapy.

As shown in FIG. 2, it was confirmed that the amount of PCNT mostly increased after the cord blood therapy regardless of types of the cord blood although the increases were observed at different days before and after the therapy.

Figure 3:
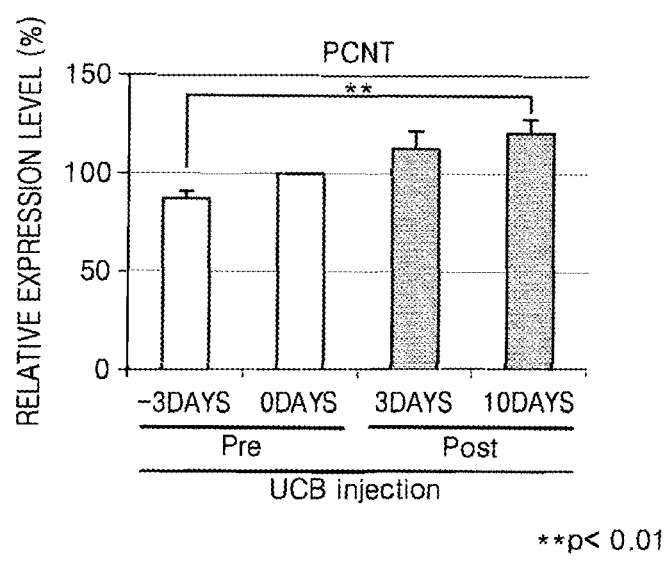
FIG. 3 is a graph illustrating changes in the expression level of PCNT before and after cord blood therapy by summing the results of all of the infants.

FIG. 3 is a graph illustrating changes in expression levels of PCNT before and after the cord blood therapy by summing the results of all of the infants shown in FIG. 2.

As shown in FIG. 3, it was confirmed that the expression level of PCNT increased at 3 days or 10 days after the cord blood therapy and the results were significant.

Thus, when the infants with cerebral palsy were treated with the cord blood, it was confirmed that the expression level of PCNT significantly increased.

Example 3: Identification of Change of PCNT in Central Nervous System Disease Animal Model 3-1. Preparation of Cerebral Palsy-Induced Mouse Model A hypoxic ischemia (HI) model was induced in 7-day-old ICR mice to prepare a cerebral palsy-induced mouse model. A right common carotid artery of a 7-day-old mouse was tied with 5-0 blue nylon, placed in a sealed container, and maintained at 8% of $O_2$ and 92% of $N_2$, at 37° C. to induce hypoxic ischemia for 1 hour. At 6 days after preparing the HI model, the degree of damage to the brain tissue was visually observed and mice damaged by 50% or more were excluded.

3-2. Administration of Cord Blood to Cerebral Palsy-Induced Mouse Model

Cord blood for research purposes donated from iCORD, a cord blood bank of CHA Medical Center, was used. The cord blood for research purposes was centrifuged at 2200 rpm to separate the cord blood into an erythrocytes, a layer of monocytes, and plasma. The plasma was separately stored, and the monocyte layer was separated using FICOLL™ (Pharmacia Corp., USA). Particularly, the erythrocytes and the monocyte layer, except for plasma, were diluted with PBS and centrifuged above FICOLL™ at 2200 rpm for 20 minutes. According to the principles of FICOLL™, erythrocytes heavier than FICOLL™ sank to the bottom below FICOLL™ and the monocyte layer is located on FICOLL™. Only the separated monocyte layer was collected and immediately added to 100 µl of a saline solution at a concentration of $4 \times 10^5$ cells/10 g. The prepared cord blood monocytes were randomly administered intraperitoneally to mice at 7 days after preparing the cerebral palsy-induced mouse model.

3-3. Identification of Change in Expression of PCNT in Brain Tissue

The cerebral palsy-induced mice were sacrificed by removing blood at one week after administering the cord blood monocytes, and brain tissue was excised. The excised brain tissue was lysed using a lysis buffer and centrifuged to separate proteins therefrom. Changes of the expression level of PCNT contained in 30 µg of the separated proteins were identified by Western blotting.

Figure 4:
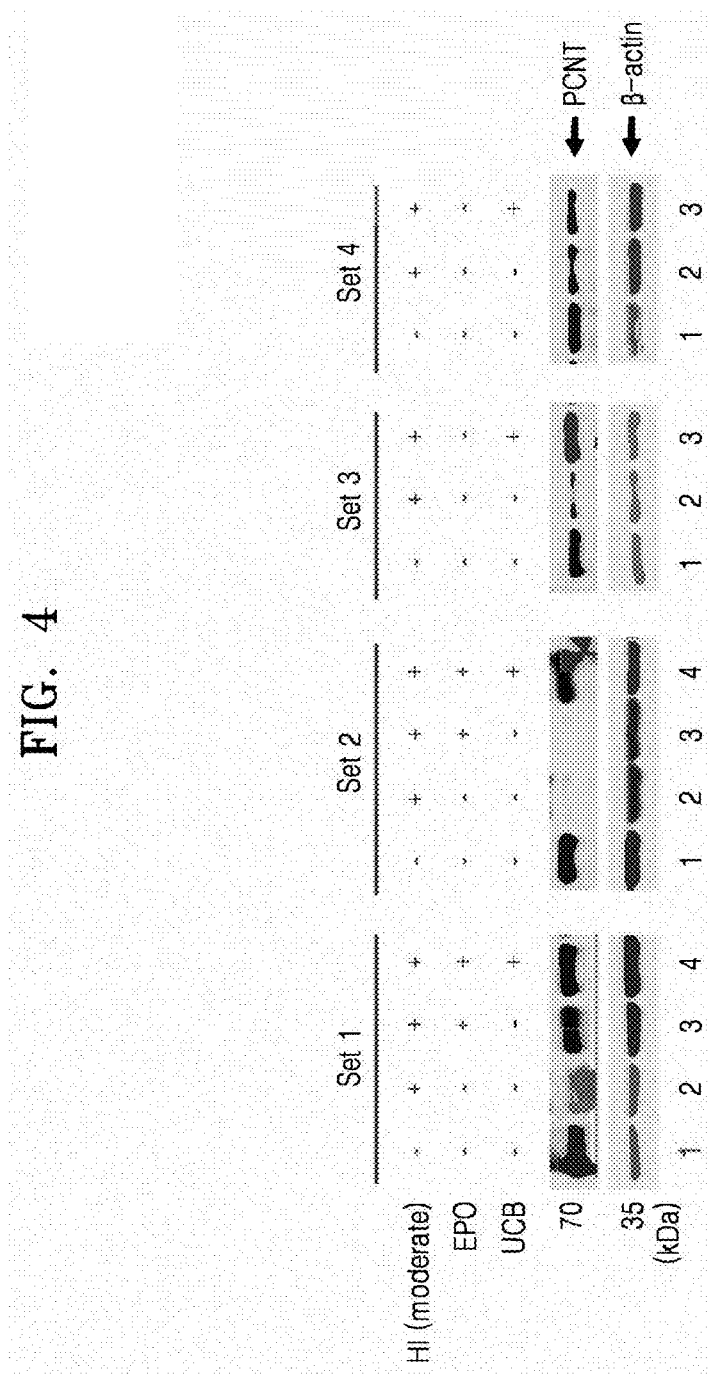
FIG. 4 shows expression levels of PCNT in a mouse model of cerebral palsy after cord blood monocytes (UCB) were administered, each measured four times. A model administered with EPO was used as a control group.

FIG. 4 shows expression levels of PCNT, identified for times, in a cerebral palsy-induced mouse model after cord blood monocytes (UCB) were administered. A model administered with EPO was used as a comparative group.

As shown in FIG. 4, it was confirmed that the expression level of PCNT increased in the cerebral palsy-induced mouse model administered with the cord blood, and it was also confirmed that the expression level of PCNT increased by the cord blood when compared with the EPM-administered model, as the comparative group.

Figure 5:
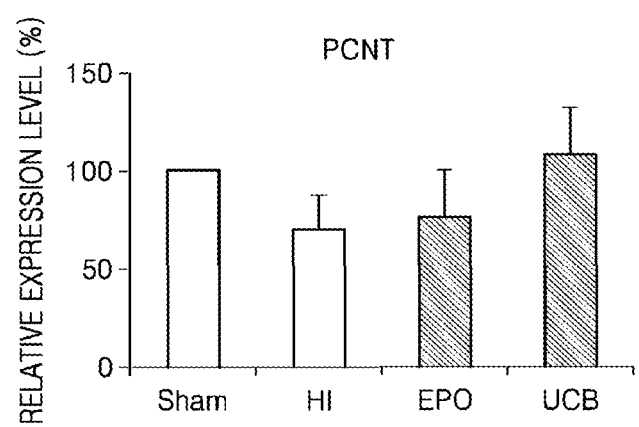
FIG. 5 is a graph illustrating changes in the expression levels of PCNT of FIG. 4, expressed as percentages, relative to a Sham model in which cerebral palsy was not induced and to which cord blood was not administered.

FIG. 5 is a graph illustrating changes of the expression level of PCNT of FIG. 4, expressed as percentage, relative to a Sham model in which the cerebral palsy was not induced and to which the cord blood was not administered.

As shown in FIG. 5, the expression level of PCNT in the cerebral palsy-induced mouse model administered with the cord blood was far higher than that of the Sham model including normal mice to which the cord blood was not administered.

Example 4: Verification of Difference in Amounts of PCNT Present in Plasma of Cord Blood, Normal Individuals, Normal Individuals, and Infants with Cerebral Palsy 4-1. Separation of Plasma from Cord Blood, Blood of Normal Individuals, and Blood of Infants with Cerebral Palsy Cord blood for research purposes donated from iCORD was centrifuged and only plasma was separated therefrom and cryopreserved in a cryocooler at −80° C. 3 cc of blood of each of normal female and male individuals between ages of 2 to 30 was centrifuged and only plasma was separated therefrom, and blood of infants with cerebral palsy in hospital obtained before cord blood therapy was centrifuged and only plasma was separated therefrom. Two plasmas were cryopreserved. Table 5 shows information on normal individuals, selected as a comparative group, and infants with cerebral palsy to identify expression of PCNT contained in cord blood.

TABLE 5

|  | Gender | Age |
|---|---|---|
| Normal individual 1 | Female | 28 |
| Normal individual 2 | Male | 31 |
| Infant with cerebral palsy 1 | Male | 2 |
| Infant with cerebral palsy 2 | Male | 3 |

4-2. Identification of Expression Level of PCNT Included in Plasma of Cord Blood, Normal Individual, and Infants with Cerebral Palsy The plasma cryopreserved according to Example 4-1 was slowly thawed on ice and diluted with PBS at 5:1. The diluted sample was quantified using a BradFord reagent and 30 μg of the sample was subjected to Western blotting.

Figure 6:
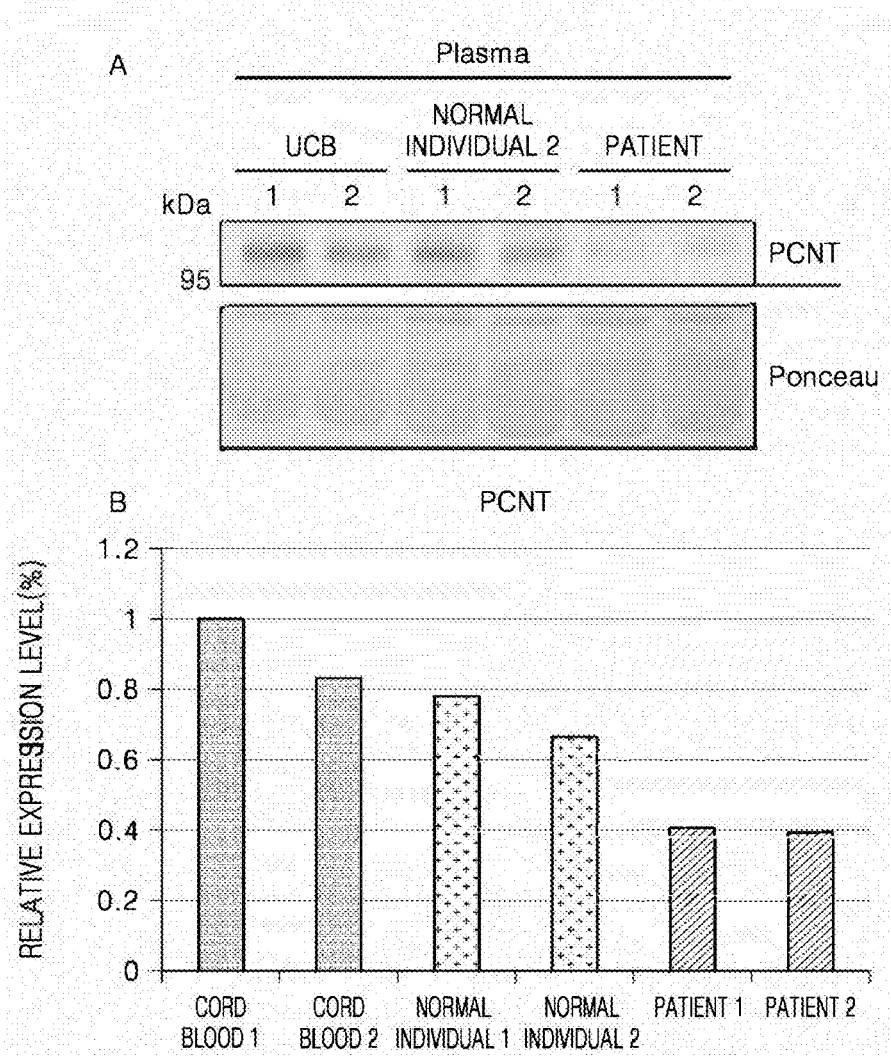
FIG. 6A shows expression levels of PCNT in plasma samples of cord blood (UCB), normal individuals, and infants with cerebral palsy.
FIG. 6B is a graph illustrating relative expression levels (%) of PCNT in plasma samples of cord blood (UCB), normal individuals, and infants with cerebral palsy with respect to cord blood sample No. 1.

FIG. 6A shows expression levels of PCNT in plasma samples of cord blood (UCB), normal individuals, and infants with cerebral palsy. FIG. 6B is a graph illustrating relative expression levels (%) of PCNT in plasma samples of cord blood (UCB), normal individuals, and infants with cerebral palsy with respect to the sample of cord blood No. 1.

As shown in FIGS. 6A and 6B, the expression levels of PCNT in the plasma of the infants with cerebral palsy were significantly lower than those of the normal individuals, and it was identified the expression levels of PCNT were the highest in the cord blood. Because there was no reference protein in plasma, it was confirmed that PCNT was most expressed in the cord blood even when the expression level of PCNT was converted to % based on a band stained with Ponceau.

Example 5: Identification of Cell Type Expressing PCNT in Cord Blood

Cord blood is blood present in umbilical cord tissue and includes a large amount of hematopoietic stem cells. The hematopoietic stem cells, as main elements of blood, are potential cells capable of differentiating into monocytes, macrophages, platelet cells, and lymphoid cells such as T-cells, B-cells, and NK cells generated in bone marrow. Thus, types of cells expressing PCNT were identified among the cells included in the cord blood. Information on the cells expressing PCNT was identified from GeneCards website (http://www.genecards.org/).

Figure 7:
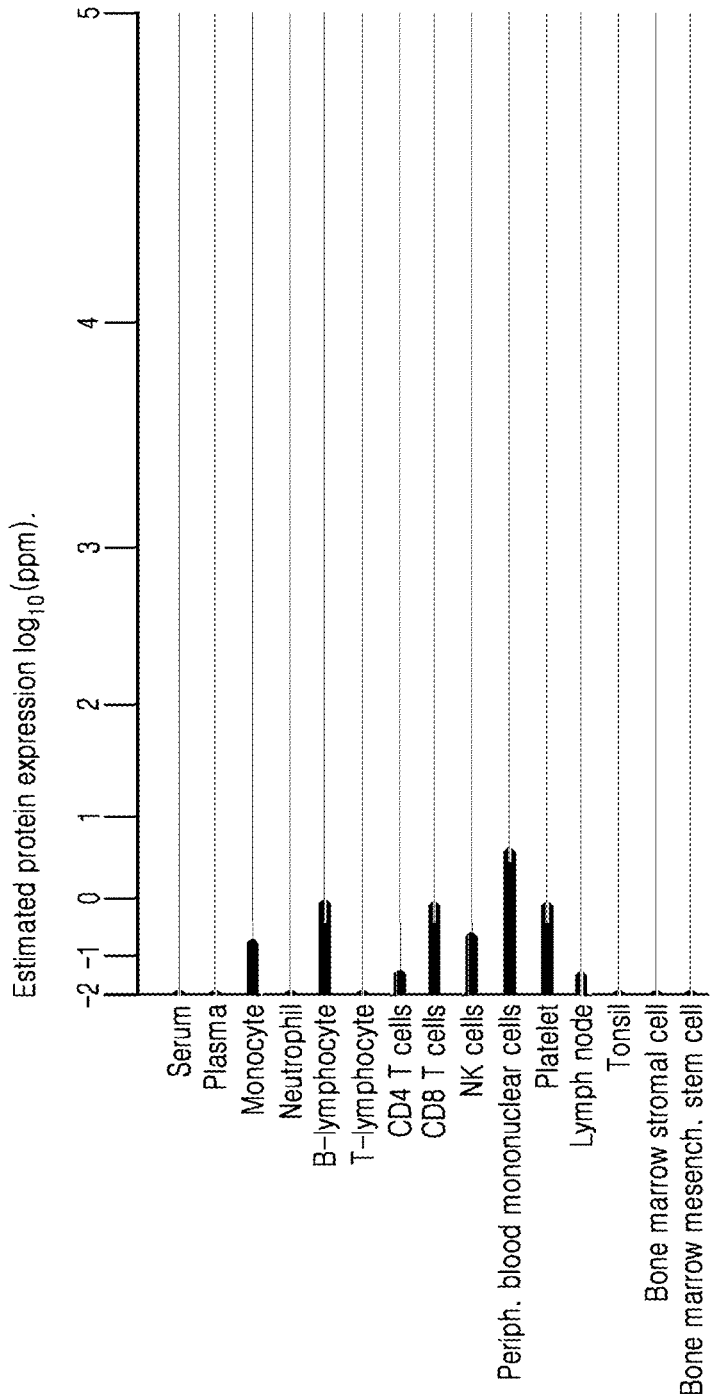
FIG. 7 is a graph illustrating expression levels of PCNT ($Log_{10}$, ppm) of respective elements of cord blood, i.e., serum, plasma, monocytes, neutrophils, B-lymphocytes, T-lymphocytes, CD4 T cells, CD8 T cells, NK cells, peripheral blood mononuclear cells (PBMCs), platelets, lymphocytes, tonsils, bone marrow stromal cells, and bone marrow mesenchymal stem cells.

FIG. 7 is a graph illustrating expression levels of PCNT ($Log_{10}$, ppm) of respective elements of the cord blood, i.e., serum, plasma, monocytes, neutrophils, B-lymphocytes, T-lymphocytes, CD4 T cells, CD8 T cells, NK cells, peripheral blood mononuclear cells (PBMCs), platelets, lymphocytes, tonsils, bone marrow stromal cells, and bone marrow mesenchymal stem cells.

As shown in FIG. 7, it was confirmed that PCNT was secreted by monocytes, B-lymphocytes, CD4 T cells, CD8 T cells, NK cells, peripheral blood mononuclear cells, platelets, and lymphocytes, among the cells contained in the cord blood. Among them, the expression level of PCNT was the highest in the peripheral blood mononuclear cells (PBMCs).

Example 6: Identification of Therapeutic Effect of Cord Blood on Central Nervous System Disease Autologous cord blood therapy was performed on infants with cerebral palsy to identify whether the cord blood therapy is actually effective on treating a central nervous system disease of patients with the central nervous system disease.

In the cord blood cell therapy, a leukocyte concentrate, which was prepared by removing erythrocytes and plasma from the blood and cryopreserved, was used as the cord blood. Before the therapy, the cryopreserved leukocyte concentrate was thawed in a water bath at 37° C. and washed with a diluted solution including 10% dextran-40 (100 g of dextran-40/1 l of water) and 5% albumin (50 g of albumin/1 l of water) in an equal volume. The washed leukocyte concentrate was suspended in 10 ml of a mixed solution in which 10% dextran-40 and 5% albumin were diluted in an equal volume, such that a minimum number of nucleated cells was $3 \times 10^7$ cells/kg, and the suspension was administered via intravenous injection at a dose of 15 ml to 30 ml.

Table 6 shows genders of selected infants with cerebral palsy, disease names, and function evaluation results after the cord blood therapy to identify therapeutic effects of the cord blood.

As shown in Table 6, it was confirmed that functions were mostly improved in the 13 infants with cerebral palsy after the cord blood therapy.

TABLE 6

| No. | Gender | Disease name | Evaluation of function after autologous cord blood therapy (Auto UCB) |
|---|---|---|---|
| 1 | Female | cerebral palsy | Decrease in stiffness of muscle in both lower limbs and able to stretch hands after therapy |
| 2 | Male | cerebral palsy | Improvement in ability to maintain midline of neck and decrease in overall rigidity after therapy |
| 3 | Female | cerebral palsy | Decrease in ataxic movement of neck and improvement in ability to move both hands in a prone position due to improved body strength after therapy |
| 4 | Male | cerebral palsy | Decrease in ataxic movement of the whole body and improvement in selective movement of upper limbs after therapy |
| 5 | Male | cerebral palsy | Decrease in ataxic movement and improvement in ability to roll over with little help after therapy |
| 6 | Female | cerebral palsy | Improvement in ability to stand while holding after the therapy and discharge from hospital despite difficulty in maintaining a standing posture before the therapy |
| 7 | Female | cerebral palsy | Improvement in balance and posture during walking and increase in walking distance after therapy |
| 8 | Male | cerebral palsy | Increased interest in objects and puzzle building observed after therapy |
| 9 | Male | cerebral palsy | Improvement in ability to roll over with little help and maintain a sitting posture for about 10 seconds with both arms supported after therapy |
| 10 | Male | cerebral palsy | Improvement in ability to maintain a standing posture while holding a bar and improvement in walking with both hands after therapy |
| 11 | Male | cerebral palsy | Improvement in ability to walk with both hands and wearing braces after therapy |
| 12 | Male | cerebral palsy | Improvement in stair-climbing ability after therapy, compared to before therapy |
| 13 | Male | cerebral palsy | Maintaining a sitting posture for a longer time due to improved body balance after therapy |

Infant Nos. 5, 11, and 13 with cerebral palsy were evaluated, at 2 to 4 months after the cord blood therapy, by The Gross Motor Function Classification System (GMFCS), Bayley Scales of Infant Development (BSID) II motor, and BSID II mental.

Figure 8:
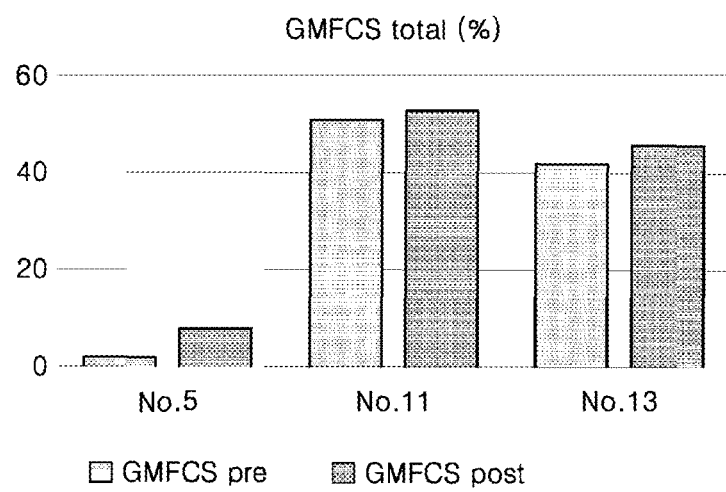
FIG. 8 is a graph illustrating GMFCS evaluation results (GMFCS total (%)) of infant Nos. 5, 11, and 13 with cerebral palsy before (GMFCS_pre) and after (GMFCS_post) cord blood therapy.

FIG. 8 is a graph illustrating GMFCS evaluation results (GMFCS total (%)) of infant Nos. 5, 11, and 13 with cerebral palsy before (GMFCS_pre) and after (GMFCS_post) the cord blood therapy.

Figure 9:
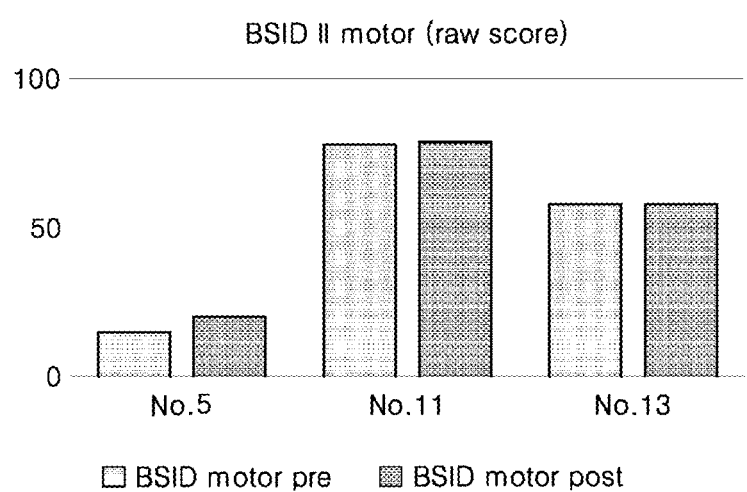
FIG. 9 is a graph illustrating BSID II motor evaluation results of infant Nos. 5, 11, and 13 with cerebral palsy before (BSID_Motor_pre) and after (BSID_Motor_post) cord blood therapy.

FIG. 9 is a graph illustrating BSID II motor evaluation results of infant Nos. 5, 11, and 13 with cerebral palsy before (BSID_Motor_pre) and after (BSID_Motor_post) the cord blood therapy.

Figure 10:
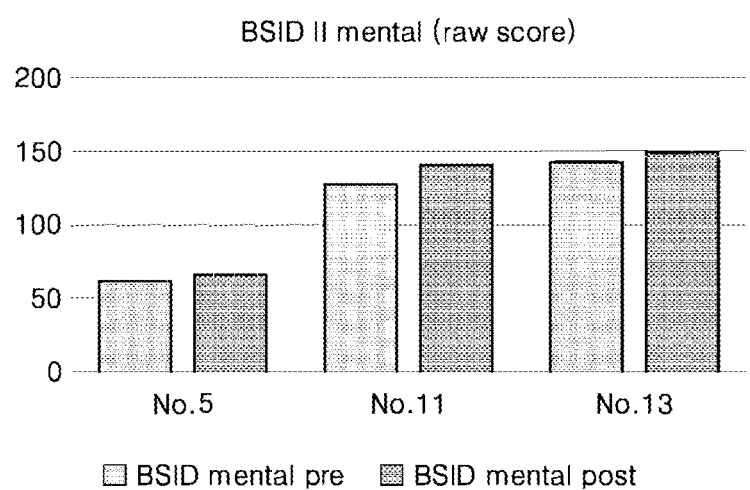
FIG. 10 is a graph illustrating BSID II mental evaluation results of infant Nos. 5, 11, and 13 with cerebral palsy before (BSID_Mental_pre) and after (BSID_Mental_post) cord blood therapy.

FIG. 10 is a graph illustrating BSID II mental evaluation results of infant Nos. 5, 11, and 13 with cerebral palsy before (BSID_Mental_pre) and after (BSID_Mental_post) the cord blood therapy.

As shown in FIGS. 8 to 10, as a result of performing the GMFCS, BSID II motor, BSID II mental tests on the infants with cerebral palsy before and after the cord blood therapy, alleviation was observed after the therapy.

INDUSTRIAL APPLICABILITY

The PCNT protein was identified as a target protein for treating or diagnosing a central nervous system disease, and thus the PCNT protein may be used as a target for diagnosing a central nervous system disease at an early stage and for developing a therapeutic agent for the central nervous system disease.

Thus, the central nervous system disease may be effectively prevented or treated by using the composition including cord blood or cord blood-derived cells expressing or secreting PCNT.

Also, the central nervous system disease may be diagnosed by using the composition or kit including an agent of measuring a level of PCNT protein or mRNA of a gene thereof.

In addition, information required for diagnosing the central nervous system disease may be analyzed by measuring an expression level or activity level of the PCNT protein or the gene thereof.

Also, a candidate substance for a therapeutic agent to treat the central nervous system disease may be screened by contacting cells expressing the PCNT protein with a test substance and measuring an expression level or activity of the PCNT protein.

The invention claimed is:

1. A method for treating a subject having central nervous system disease, the method comprising: administering to the subject an effective amount of a composition comprising:
   as an active ingredient, leukocytes in cord blood expressing or secreting the amino acid sequence consisting of SEQ ID NO: 1, and erythropoietin (EPO),
   wherein an expression level of the amino acid sequence consisting of SEQ ID NO: 1 is reduced in the subject having central nervous system disease before the administering the composition as compared with that of a normal individual.

2. The method of claim 1, wherein the central nervous system disease is selected from the group consisting of cerebral palsy, brain damage, traumatic brain injury, ischemic brain injury, concussion, cerebral contusion, cerebral apoplexy, cerebral infarction, cerebral hemorrhage, Parkinson's disease, Alzheimer's disease, Huntington's chorea, stroke, dementia, Lou Gehrig's disease, Pick disease, Creutzfeldt-Jakob disease, amyotrophic lateral sclerosis, primary lateral sclerosis, degenerative ataxia, multiple sclerosis, nervous system dysfunction, hypomnesis, epilepsy, encephalitis, prion disease, and neuropathy.

3. The method of claim 1, wherein the cord blood is autologous cord blood or allogeneic cord blood.

* * * * *

SEQUENCE LISTING

```
<160> NUMBER OF SEQ ID NOS: 1

<210> SEQ ID NO 1
<211> LENGTH: 3229
<212> TYPE: PRT
<213> ORGANISM: Homo sapiens

<400> SEQUENCE: 1

Met Phe Thr Val Ser Asp His Pro Pro Glu Gln His Gly Met Phe Thr
1               5                   10                  15

Val Gly Asp His Pro Pro Glu Gln Arg Gly Met Phe Thr Val Ser Asp
                20                  25                  30

His Pro Pro Glu Gln His Gly Met Phe Thr Val Ser Asp His Pro Pro
            35                  40                  45

Glu Gln Arg Gly Met Phe Thr Ile Ser Asp His Gln Pro Glu Gln Arg
        50                  55                  60

Gly Met Phe Thr Val Ser Asp His Thr Pro Glu Gln Arg Gly Ile Phe
65                  70                  75                  80

Thr Ile Ser Asp His Pro Ala Glu Gln Arg Gly Met Phe Thr Lys Glu
                85                  90                  95

Cys Glu Gln Glu Cys Glu Leu Ala Ile Thr Asp Leu Glu Ser Gly Arg
            100                 105                 110

Glu Asp Glu Ala Gly Leu His Gln Ser Gln Ala Val His Gly Leu Glu
        115                 120                 125

Leu Glu Ala Leu Arg Leu Ser Leu Ser Asn Met His Thr Ala Gln Leu
    130                 135                 140

Glu Leu Thr Gln Ala Asn Leu Gln Lys Glu Lys Glu Thr Ala Leu Thr
145                 150                 155                 160

Glu Leu Arg Glu Met Leu Asn Ser Arg Arg Ala Gln Glu Leu Ala Leu
                165                 170                 175

Leu Gln Ser Arg Gln Gln His Glu Leu Glu Leu Leu Arg Glu Gln His
            180                 185                 190

Ala Arg Glu Lys Glu Val Val Leu Arg Cys Gly Gln Glu Ala Ala
        195                 200                 205

Glu Leu Lys Glu Lys Leu Gln Ser Glu Met Glu Lys Asn Ala Gln Ile
    210                 215                 220

Val Lys Thr Leu Lys Glu Asp Trp Glu Ser Glu Lys Asp Leu Cys Leu
225                 230                 235                 240

Glu Asn Leu Arg Lys Glu Leu Ser Ala Lys His Gln Ser Glu Met Glu
                245                 250                 255
```

```
Asp Leu Gln Asn Gln Phe Gln Lys Glu Leu Ala Glu Gln Arg Ala Glu
            260                 265                 270

Leu Glu Lys Ile Phe Gln Asp Lys Asn Gln Ala Glu Arg Ala Leu Arg
        275                 280                 285

Asn Leu Glu Ser His His Gln Ala Ala Ile Glu Lys Leu Arg Glu Asp
        290                 295                 300

Leu Gln Ser Glu His Gly Arg Cys Leu Glu Asp Leu Glu Phe Lys Phe
305                 310                 315                 320

Lys Glu Ser Glu Lys Glu Lys Gln Leu Glu Leu Glu Asn Leu Gln Ala
                325                 330                 335

Ser Tyr Glu Asp Leu Lys Ala Gln Ser Gln Glu Glu Ile Arg Arg Leu
            340                 345                 350

Trp Ser Gln Leu Asp Ser Ala Arg Thr Ser Arg Gln Glu Leu Ser Glu
        355                 360                 365

Leu His Glu Gln Leu Leu Ala Arg Thr Ser Arg Val Glu Asp Leu Glu
        370                 375                 380

Gln Leu Lys Gln Arg Glu Lys Thr Gln His Glu Ser Glu Leu Glu Gln
385                 390                 395                 400

Leu Arg Ile Tyr Phe Glu Lys Lys Leu Arg Asp Ala Glu Lys Thr Tyr
                405                 410                 415

Gln Glu Asp Leu Thr Leu Leu Gln Gln Arg Leu Gln Gly Ala Arg Glu
            420                 425                 430

Asp Ala Leu Leu Asp Ser Val Glu Val Gly Leu Ser Cys Val Gly Leu
        435                 440                 445

Glu Glu Lys Pro Glu Lys Gly Arg Lys Asp His Val Asp Glu Leu Glu
        450                 455                 460

Pro Glu Arg His Lys Glu Ser Leu Pro Arg Phe Gln Ala Glu Leu Glu
465                 470                 475                 480

Glu Ser His Arg His Gln Leu Glu Ala Leu Glu Ser Pro Leu Cys Ile
                485                 490                 495

Gln His Glu Gly His Val Ser Asp Arg Cys Cys Val Glu Thr Ser Ala
            500                 505                 510

Leu Gly His Glu Trp Arg Leu Glu Pro Ser Glu Gly His Ser Gln Glu
        515                 520                 525

Leu Pro Trp Val His Leu Gln Gly Val Gln Asp Gly Asp Leu Glu Ala
        530                 535                 540

Asp Thr Glu Arg Ala Ala Arg Val Leu Gly Leu Glu Thr Glu His Lys
545                 550                 555                 560

Val Gln Leu Ser Leu Leu Gln Thr Glu Leu Lys Glu Glu Ile Glu Leu
                565                 570                 575

Leu Lys Ile Glu Asn Arg Asn Leu Tyr Gly Lys Leu Gln His Glu Thr
            580                 585                 590

Arg Leu Lys Asp Asp Leu Glu Lys Val Lys His Asn Leu Ile Glu Asp
        595                 600                 605

His Gln Lys Glu Leu Asn Asn Ala Lys Gln Lys Thr Glu Leu Met Lys
        610                 615                 620

Gln Glu Phe Gln Arg Lys Glu Thr Asp Trp Lys Val Met Lys Glu Glu
625                 630                 635                 640

Leu Gln Arg Glu Ala Glu Gly Lys Leu Thr Leu Met Leu Leu Glu Leu
                645                 650                 655

Arg Glu Lys Ala Glu Ser Glu Lys Gln Thr Ile Ile Asn Lys Phe Glu
            660                 665                 670
```

```
Leu Arg Glu Ala Glu Met Arg Gln Leu Gln Asp Gln Ala Ala Gln
            675                 680                 685

Ile Leu Asp Leu Glu Arg Ser Leu Thr Glu Gln Gln Gly Arg Leu Gln
    690                 695                 700

Gln Leu Glu Gln Asp Leu Thr Ser Asp Asp Ala Leu His Cys Ser Gln
705                 710                 715                 720

Cys Gly Arg Glu Pro Pro Thr Ala Gln Asp Gly Glu Leu Ala Ala Leu
                725                 730                 735

His Val Lys Glu Asp Cys Ala Leu Gln Leu Met Leu Ala Arg Ser Arg
            740                 745                 750

Phe Leu Glu Glu Arg Lys Glu Ile Thr Glu Lys Phe Ser Ala Glu Gln
    755                 760                 765

Asp Ala Phe Leu Gln Glu Ala Gln Gln His Ala Arg Glu Leu Gln
770                 775                 780

Leu Leu Gln Glu Arg His Gln Gln Leu Leu Ser Val Thr Ala Glu
785                 790                 795                 800

Leu Glu Ala Arg His Gln Ala Ala Leu Gly Glu Leu Thr Ala Ser Leu
                805                 810                 815

Glu Ser Lys Gln Gly Ala Leu Leu Ala Ala Arg Val Ala Glu Leu Gln
            820                 825                 830

Thr Lys His Ala Ala Asp Leu Gly Ala Leu Glu Thr Arg His Leu Ser
            835                 840                 845

Ser Leu Asp Ser Leu Glu Ser Cys Tyr Leu Ser Glu Phe Gln Thr Ile
    850                 855                 860

Arg Glu Glu His Arg Gln Ala Leu Glu Leu Leu Arg Ala Asp Phe Glu
865                 870                 875                 880

Glu Gln Leu Trp Lys Lys Asp Ser Leu His Gln Thr Ile Leu Thr Gln
                885                 890                 895

Glu Leu Glu Lys Leu Lys Arg Lys His Glu Gly Leu Gln Ser Val
    900                 905                 910

Arg Asp His Leu Arg Thr Glu Val Ser Thr Glu Leu Ala Gly Thr Val
            915                 920                 925

Ala His Glu Leu Gln Gly Val His Gln Gly Glu Phe Gly Ser Glu Lys
            930                 935                 940

Lys Thr Ala Leu His Glu Lys Glu Thr Leu Arg Leu Gln Ser Ala
945                 950                 955                 960

Gln Ala Gln Pro Phe His Gln Glu Lys Glu Ser Leu Ser Leu Gln
                965                 970                 975

Leu Gln Lys Lys Asn His Gln Val Gln Gln Leu Lys Asp Gln Val Leu
            980                 985                 990

Ser Leu Ser His Glu Ile Glu Glu Cys Arg Ser Glu Leu Glu Val Leu
            995                1000               1005

Gln Gln Arg Arg Glu Arg Glu Asn Arg Glu Gly Ala Asn Leu Leu
1010                1015               1020

Ser Met Leu Lys Ala Asp Val Asn Leu Ser His Ser Glu Arg Gly
    1025                1030                1035

Ala Leu Gln Asp Ala Leu Arg Arg Leu Leu Gly Leu Phe Gly Glu
    1040                1045                1050

Thr Leu Arg Ala Ala Val Thr Leu Arg Ser Arg Ile Gly Glu Arg
    1055                1060                1065

Val Gly Leu Cys Leu Asp Asp Ala Gly Ala Gly Leu Ala Leu Ser
    1070                1075                1080

Thr Ala Pro Ala Leu Glu Glu Thr Trp Ser Asp Val Ala Leu Pro
```

-continued

```
            1085                1090                1095
Glu Leu Asp Arg Thr Leu Ser Glu Cys Ala Glu Met Ser Ser Val
            1100                1105                1110
Ala Glu Ile Ser Ser His Met Arg Glu Ser Phe Leu Met Ser Pro
            1115                1120                1125
Glu Ser Val Arg Glu Cys Glu Gln Pro Ile Arg Arg Val Phe Gln
            1130                1135                1140
Ser Leu Ser Leu Ala Val Asp Gly Leu Met Glu Met Ala Leu Asp
            1145                1150                1155
Ser Ser Arg Gln Leu Glu Glu Ala Arg Gln Ile His Ser Arg Phe
            1160                1165                1170
Glu Lys Glu Phe Ser Phe Lys Asn Glu Glu Thr Ala Gln Val Val
            1175                1180                1185
Arg Lys His Gln Glu Leu Leu Glu Cys Leu Lys Glu Glu Ser Ala
            1190                1195                1200
Ala Lys Ala Glu Leu Ala Leu Glu Leu His Lys Thr Gln Gly Thr
            1205                1210                1215
Leu Glu Gly Phe Lys Val Glu Thr Ala Asp Leu Lys Glu Val Leu
            1220                1225                1230
Ala Gly Lys Glu Asp Ser Glu His Arg Leu Val Leu Glu Leu Glu
            1235                1240                1245
Ser Leu Arg Arg Gln Leu Gln Gln Ala Ala Gln Glu Gln Ala Ala
            1250                1255                1260
Leu Arg Glu Glu Cys Thr Arg Leu Trp Ser Arg Gly Glu Ala Thr
            1265                1270                1275
Ala Thr Asp Ala Glu Ala Arg Glu Ala Gly Thr Ala Val Thr Ala
            1280                1285                1290
Ala His Lys Asp Ser Ala Leu Arg Lys Glu Val Glu Asp Leu Thr
            1295                1300                1305
Lys Glu Gln Ser Glu Thr Arg Lys Gln Ala Glu Lys Asp Arg Ser
            1310                1315                1320
Ala Leu Leu Ser Gln Met Lys Ile Leu Glu Ser Glu Leu Glu Glu
            1325                1330                1335
Gln Leu Ser Gln His Arg Gly Cys Ala Lys Gln Ala Glu Ala Val
            1340                1345                1350
Thr Ala Leu Glu Gln Gln Val Ala Ser Leu Asp Lys His Leu Arg
            1355                1360                1365
Asn Gln Arg Gln Phe Met Asp Glu Gln Ala Ala Glu Arg Glu His
            1370                1375                1380
Glu Arg Glu Glu Phe Gln Gln Glu Ile Gln Arg Leu Glu Gly Gln
            1385                1390                1395
Leu Arg Gln Ala Ala Lys Pro Gln Pro Trp Gly Pro Arg Asp Ser
            1400                1405                1410
Gln Gln Ala Pro Leu Asp Gly Glu Val Glu Leu Leu Gln Gln Lys
            1415                1420                1425
Leu Arg Glu Lys Leu Asp Glu Phe Asn Glu Leu Ala Ile Gln Lys
            1430                1435                1440
Glu Ser Ala Asp Arg Gln Val Leu Met Gln Glu Glu Ile Lys
            1445                1450                1455
Arg Leu Glu Glu Met Asn Ile Asn Ile Arg Lys Lys Val Ala Gln
            1460                1465                1470
Leu Gln Glu Glu Val Glu Lys Gln Lys Asn Ile Val Lys Gly Leu
            1475                1480                1485
```

```
Glu Gln Asp Lys Glu Val Leu Lys Lys Gln Gln Met Ser Ser Leu
    1490            1495            1500

Leu Leu Ala Ser Thr Leu Gln Ser Thr Leu Asp Ala Gly Arg Cys
    1505            1510            1515

Pro Glu Pro Pro Ser Gly Ser Pro Pro Glu Gly Pro Glu Ile Gln
    1520            1525            1530

Leu Glu Val Thr Gln Arg Ala Leu Leu Arg Arg Glu Ser Glu Val
    1535            1540            1545

Leu Asp Leu Lys Glu Gln Leu Glu Lys Met Lys Gly Asp Leu Glu
    1550            1555            1560

Ser Lys Asn Glu Glu Ile Leu His Leu Asn Leu Lys Leu Asp Met
    1565            1570            1575

Gln Asn Ser Gln Thr Ala Val Ser Leu Arg Glu Leu Glu Glu Glu
    1580            1585            1590

Asn Thr Ser Leu Lys Val Ile Tyr Thr Arg Ser Ser Glu Ile Glu
    1595            1600            1605

Glu Leu Lys Ala Thr Ile Glu Asn Leu Gln Glu Asn Gln Lys Arg
    1610            1615            1620

Leu Gln Lys Glu Lys Ala Glu Ile Glu Gln Leu His Glu Val
    1625            1630            1635

Ile Glu Lys Leu Gln His Glu Leu Ser Leu Met Gly Pro Val Val
    1640            1645            1650

His Glu Val Ser Asp Ser Gln Ala Gly Ser Leu Gln Ser Glu Leu
    1655            1660            1665

Leu Cys Ser Gln Ala Gly Gly Pro Arg Gly Gln Ala Leu Gln Gly
    1670            1675            1680

Glu Leu Glu Ala Ala Leu Glu Ala Lys Glu Ala Leu Ser Arg Leu
    1685            1690            1695

Leu Ala Asp Gln Glu Arg Arg His Ser Gln Ala Leu Glu Ala Leu
    1700            1705            1710

Gln Gln Arg Leu Gln Gly Ala Glu Glu Ala Ala Glu Leu Gln Leu
    1715            1720            1725

Ala Glu Leu Glu Arg Asn Val Ala Leu Arg Glu Ala Glu Val Glu
    1730            1735            1740

Asp Met Ala Ser Arg Ile Gln Glu Phe Glu Ala Ala Leu Lys Ala
    1745            1750            1755

Lys Glu Ala Thr Ile Ala Glu Arg Asn Leu Glu Ile Asp Ala Leu
    1760            1765            1770

Asn Gln Arg Lys Ala Ala His Ser Ala Glu Leu Glu Ala Val Leu
    1775            1780            1785

Leu Ala Leu Ala Arg Ile Arg Arg Ala Leu Glu Gln Gln Pro Leu
    1790            1795            1800

Ala Ala Gly Ala Ala Pro Pro Glu Leu Gln Trp Leu Arg Ala Gln
    1805            1810            1815

Cys Ala Arg Leu Ser Arg Gln Leu Gln Val Leu His Gln Arg Phe
    1820            1825            1830

Leu Arg Cys Gln Val Glu Leu Asp Arg Arg Gln Ala Arg Arg Ala
    1835            1840            1845

Thr Ala His Thr Arg Val Pro Gly Ala His Pro Gln Pro Arg Met
    1850            1855            1860

Asp Gly Gly Ala Lys Ala Gln Val Thr Gly Asp Val Glu Ala Ser
    1865            1870            1875
```

-continued

His Asp Ala Ala Leu Glu Pro Val Val Pro Asp Pro Gln Gly Asp
1880               1885              1890

Leu Gln Pro Val Leu Val Thr Leu Lys Asp Ala Pro Leu Cys Lys
1895               1900              1905

Gln Glu Gly Val Met Ser Val Leu Thr Val Cys Gln Arg Gln Leu
1910               1915              1920

Gln Ser Glu Leu Leu Leu Val Lys Asn Glu Met Arg Leu Ser Leu
1925               1930              1935

Glu Asp Gly Gly Lys Gly Lys Glu Lys Val Leu Glu Asp Cys Gln
1940               1945              1950

Leu Pro Lys Val Asp Leu Val Ala Gln Val Lys Gln Leu Gln Glu
1955               1960              1965

Lys Leu Asn Arg Leu Leu Tyr Ser Met Thr Phe Gln Asn Val Asp
1970               1975              1980

Ala Ala Asp Thr Lys Ser Leu Trp Pro Met Ala Ser Ala His Leu
1985               1990              1995

Leu Glu Ser Ser Trp Ser Asp Ser Cys Asp Gly Glu Glu Pro
2000               2005              2010

Asp Ile Ser Pro His Ile Asp Thr Cys Asp Ala Asn Thr Ala Thr
2015               2020              2025

Gly Gly Val Thr Asp Val Ile Lys Asn Gln Ala Ile Asp Ala Cys
2030               2035              2040

Asp Ala Asn Thr Thr Pro Gly Gly Val Thr Asp Val Ile Lys Asn
2045               2050              2055

Trp Asp Ser Leu Ile Pro Asp Glu Met Pro Asp Ser Pro Ile Gln
2060               2065              2070

Glu Lys Ser Glu Cys Gln Asp Met Ser Leu Ser Ser Pro Thr Ser
2075               2080              2085

Val Leu Gly Gly Ser Arg His Gln Ser His Thr Ala Glu Ala Gly
2090               2095              2100

Pro Arg Lys Ser Pro Val Gly Met Leu Asp Leu Ser Ser Trp Ser
2105               2110              2115

Ser Pro Glu Val Leu Arg Lys Asp Trp Thr Leu Glu Pro Trp Pro
2120               2125              2130

Ser Leu Pro Val Thr Pro His Ser Gly Ala Leu Ser Leu Cys Ser
2135               2140              2145

Ala Asp Thr Ser Leu Gly Asp Arg Ala Asp Thr Ser Leu Pro Gln
2150               2155              2160

Thr Gln Gly Pro Gly Leu Leu Cys Ser Pro Gly Val Ser Ala Ala
2165               2170              2175

Ala Leu Ala Leu Gln Trp Ala Glu Ser Pro Pro Ala Asp Asp His
2180               2185              2190

His Val Gln Arg Thr Ala Val Glu Lys Asp Val Glu Asp Phe Ile
2195               2200              2205

Thr Thr Ser Phe Asp Ser Gln Glu Thr Leu Ser Ser Pro Pro Pro
2210               2215              2220

Gly Leu Glu Gly Lys Ala Asp Arg Ser Glu Lys Ser Asp Gly Ser
2225               2230              2235

Gly Phe Gly Ala Arg Leu Ser Pro Gly Ser Gly Gly Pro Glu Ala
2240               2245              2250

Gln Thr Ala Gly Pro Val Thr Pro Ala Ser Ile Ser Gly Arg Phe
2255               2260              2265

Gln Pro Leu Pro Glu Ala Met Lys Glu Lys Glu Val Arg Pro Lys

```
              2270                2275                2280

His Val Lys Ala Leu Leu Gln Met Val Arg Asp Glu Ser His Gln
         2285                2290                2295

Ile Leu Ala Leu Ser Glu Gly Leu Ala Pro Pro Ser Gly Glu Pro
         2300                2305                2310

His Pro Pro Arg Lys Glu Asp Glu Ile Gln Asp Ile Ser Leu His
         2315                2320                2325

Gly Gly Lys Thr Gln Glu Val Pro Thr Ala Cys Pro Asp Trp Arg
         2330                2335                2340

Gly Asp Leu Leu Gln Val Val Gln Glu Ala Phe Glu Lys Glu Gln
         2345                2350                2355

Glu Met Gln Gly Val Glu Leu Gln Pro Arg Leu Ser Gly Ser Asp
         2360                2365                2370

Leu Gly Gly His Ser Ser Leu Leu Glu Arg Leu Glu Lys Ile Ile
         2375                2380                2385

Arg Glu Gln Gly Asp Leu Gln Glu Lys Ser Leu Glu His Leu Arg
         2390                2395                2400

Leu Pro Asp Arg Ser Ser Leu Leu Ser Glu Ile Gln Ala Leu Arg
         2405                2410                2415

Ala Gln Leu Arg Met Thr His Leu Gln Asn Gln Glu Lys Leu Gln
         2420                2425                2430

His Leu Arg Thr Ala Leu Thr Ser Ala Glu Ala Arg Gly Ser Gln
         2435                2440                2445

Gln Glu His Gln Leu Arg Arg Gln Val Glu Leu Leu Ala Tyr Lys
         2450                2455                2460

Val Glu Gln Glu Lys Cys Ile Ala Gly Asp Leu Gln Lys Thr Leu
         2465                2470                2475

Ser Glu Glu Gln Glu Lys Ala Asn Ser Val Gln Lys Leu Leu Ala
         2480                2485                2490

Ala Glu Gln Thr Val Val Arg Asp Leu Lys Ser Asp Leu Cys Glu
         2495                2500                2505

Ser Arg Gln Lys Ser Glu Gln Leu Ser Arg Ser Leu Cys Glu Val
         2510                2515                2520

Gln Gln Glu Val Leu Gln Leu Arg Ser Met Leu Ser Ser Lys Glu
         2525                2530                2535

Asn Glu Leu Lys Ala Ala Leu Gln Glu Leu Glu Ser Glu Gln Gly
         2540                2545                2550

Lys Gly Arg Ala Leu Gln Ser Gln Leu Glu Glu Glu Gln Leu Arg
         2555                2560                2565

His Leu Gln Arg Glu Ser Gln Ser Ala Lys Ala Leu Glu Glu Leu
         2570                2575                2580

Arg Ala Ser Leu Glu Thr Gln Arg Ala Gln Ser Ser Arg Leu Cys
         2585                2590                2595

Val Ala Leu Lys His Glu Gln Thr Ala Lys Asp Asn Leu Gln Lys
         2600                2605                2610

Glu Leu Arg Ile Glu His Ser Arg Cys Glu Ala Leu Leu Ala Gln
         2615                2620                2625

Glu Arg Ser Gln Leu Ser Glu Leu Gln Lys Asp Leu Ala Ala Glu
         2630                2635                2640

Lys Ser Arg Thr Leu Glu Leu Ser Glu Ala Leu Arg His Glu Arg
         2645                2650                2655

Leu Leu Thr Glu Gln Leu Ser Gln Arg Thr Gln Glu Ala Cys Val
         2660                2665                2670
```

```
His Gln Asp Thr Gln Ala His His Ala Leu Leu Gln Lys Leu Lys
    2675                2680                2685

Glu Glu Lys Ser Arg Val Val Asp Leu Gln Ala Met Leu Glu Lys
    2690                2695                2700

Val Gln Gln Gln Ala Leu His Ser Gln Gln Gln Leu Glu Ala Glu
    2705                2710                2715

Ala Gln Lys His Cys Glu Ala Leu Arg Arg Glu Lys Glu Val Ser
    2720                2725                2730

Ala Thr Leu Lys Ser Thr Val Glu Ala Leu His Thr Gln Lys Arg
    2735                2740                2745

Glu Leu Arg Cys Ser Leu Glu Arg Glu Arg Lys Pro Ala Trp
    2750                2755                2760

Leu Gln Ala Glu Leu Glu Gln Ser His Pro Arg Leu Lys Glu Gln
    2765                2770                2775

Glu Gly Arg Lys Ala Ala Arg Arg Ser Ala Glu Ala Arg Gln Ser
    2780                2785                2790

Pro Ala Ala Ala Glu Gln Trp Arg Lys Trp Gln Arg Asp Lys Glu
    2795                2800                2805

Lys Leu Arg Glu Leu Glu Leu Gln Arg Gln Arg Asp Leu His Lys
    2810                2815                2820

Ile Lys Gln Leu Gln Gln Thr Val Arg Asp Leu Glu Ser Lys Asp
    2825                2830                2835

Glu Val Pro Gly Ser Arg Leu His Leu Gly Ser Ala Arg Arg Ala
    2840                2845                2850

Ala Gly Ser Asp Ala Asp His Leu Arg Glu Gln Gln Arg Glu Leu
    2855                2860                2865

Glu Ala Met Arg Gln Arg Leu Leu Ser Ala Ala Arg Leu Leu Thr
    2870                2875                2880

Ser Phe Thr Ser Gln Ala Val Asp Arg Thr Val Asn Asp Trp Thr
    2885                2890                2895

Ser Ser Asn Glu Lys Ala Val Met Ser Leu Leu His Thr Leu Glu
    2900                2905                2910

Glu Leu Lys Ser Asp Leu Ser Arg Pro Thr Ser Ser Gln Lys Lys
    2915                2920                2925

Met Ala Ala Glu Leu Gln Phe Gln Phe Val Asp Val Leu Leu Lys
    2930                2935                2940

Asp Asn Val Ser Leu Thr Lys Ala Leu Ser Thr Val Thr Gln Glu
    2945                2950                2955

Lys Leu Glu Leu Ser Arg Ala Val Ser Lys Leu Glu Lys Leu Leu
    2960                2965                2970

Lys His His Leu Gln Lys Gly Cys Ser Pro Ser Arg Ser Glu Arg
    2975                2980                2985

Ser Ala Trp Lys Pro Asp Glu Thr Ala Pro Gln Ser Ser Leu Arg
    2990                2995                3000

Arg Pro Asp Pro Gly Arg Leu Pro Pro Ala Ala Ser Glu Glu Ala
    3005                3010                3015

His Thr Ser Asn Val Lys Met Glu Lys Leu Tyr Leu His Tyr Leu
    3020                3025                3030

Arg Ala Glu Ser Phe Arg Lys Ala Leu Ile Tyr Gln Lys Lys Tyr
    3035                3040                3045

Leu Leu Leu Leu Ile Gly Gly Phe Gln Asp Ser Glu Gln Glu Thr
    3050                3055                3060
```

-continued

```
Leu Ser Met Ile Ala His Leu Gly Val Phe Pro Ser Lys Ala Glu
3065                3070                3075

Arg Lys Ile Thr Ser Arg Pro Phe Thr Arg Phe Arg Thr Ala Val
3080                3085                3090

Arg Val Val Ile Ala Ile Leu Arg Leu Arg Phe Leu Val Lys Lys
3095                3100                3105

Trp Gln Glu Val Asp Arg Lys Gly Ala Leu Ala Gln Gly Lys Ala
3110                3115                3120

Pro Arg Pro Gly Pro Arg Ala Arg Gln Pro Gln Ser Pro Pro Arg
3125                3130                3135

Thr Arg Glu Ser Pro Pro Thr Arg Asp Val Pro Ser Gly His Thr
3140                3145                3150

Arg Asp Pro Ala Arg Gly Arg Arg Leu Ala Ala Ala Ala Ser Pro
3155                3160                3165

His Ser Gly Gly Arg Ala Thr Pro Ser Pro Asn Ser Arg Leu Glu
3170                3175                3180

Arg Ser Leu Thr Ala Ser Gln Asp Pro Glu His Ser Leu Thr Glu
3185                3190                3195

Tyr Ile His His Leu Glu Val Ile Gln Gln Arg Leu Gly Gly Val
3200                3205                3210

Leu Pro Asp Ser Thr Ser Lys Lys Ser Cys His Pro Met Ile Lys
3215                3220                3225

Gln
```